United States Patent
Lattner

(10) Patent No.: US 7,470,825 B2
(45) Date of Patent: Dec. 30, 2008

(54) REACTOR AND PROCESS FOR PRODUCING METHANOL

(75) Inventor: James R. Lattner, LaPorte, TX (US)

(73) Assignee: ExxonMobil Chemical Patents Inc., Houston, TX (US)

(*) Notice: Subject to any disclaimer, the term of this patent is extended or adjusted under 35 U.S.C. 154(b) by 0 days.

(21) Appl. No.: 11/801,451

(22) Filed: May 10, 2007

(65) Prior Publication Data

US 2007/0299145 A1  Dec. 27, 2007

Related U.S. Application Data

(60) Provisional application No. 60/816,409, filed on Jun. 26, 2006.

(51) Int. Cl.
*C07C 27/00* (2006.01)

(52) U.S. Cl. .................................................. 568/909

(58) Field of Classification Search ................. 568/909
See application file for complete search history.

(56) References Cited

U.S. PATENT DOCUMENTS

| 2,877,099 | A |   | 3/1959 | Bowles |  |
| 4,471,154 | A |   | 9/1984 | Franklin |  |
| 4,670,473 | A | * | 6/1987 | Walker et al. | 518/706 |
| 4,825,013 | A | * | 4/1989 | Quarderer et al. | 568/902.2 |
| 4,968,722 | A | * | 11/1990 | Westerterp | 518/706 |
| 4,980,380 | A | * | 12/1990 | Wong et al. | 518/714 |
| 5,219,891 | A | * | 6/1993 | Sie | 518/706 |
| 5,262,443 | A | * | 11/1993 | Topsoe et al. | 518/728 |
| 5,449,696 | A | * | 9/1995 | Dandekar et al. | 518/706 |
| 5,712,313 | A | * | 1/1998 | Kramer et al. | 518/706 |
| 6,191,174 | B1 | * | 2/2001 | Early et al. | 518/705 |
| 6,303,092 | B1 | * | 10/2001 | Anand et al. | 423/418.2 |
| 6,723,886 | B2 | * | 4/2004 | Allison et al. | 568/909 |
| 7,195,741 | B2 | * | 3/2007 | Lattner et al. | 422/141 |
| 7,232,848 | B2 | * | 6/2007 | Mohedas et al. | 518/726 |
| 2007/0021514 | A1 | * | 1/2007 | Lattner | 518/726 |
| 2007/0027220 | A1 | * | 2/2007 | Lattner | 518/726 |
| 2007/0043126 | A1 | * | 2/2007 | Lattner | 518/726 |
| 2007/0299145 | A1 | * | 12/2007 | Lattner | 518/705 |
| 2007/0299146 | A1 | * | 12/2007 | Lattner | 518/709 |

FOREIGN PATENT DOCUMENTS

| CA | 793293 | * | 8/1968 |
| EP | 026 057 |   | 3/1984 |
| GB | 2 096 603 |   | 10/1982 |
| GB | 2255516 A | * | 11/1992 |
| WO | WO 99/00182 |   | 1/1999 |

OTHER PUBLICATIONS

Wu et al. Reneng Dongli Gongcheng (2007), 22(4). 385-390.*
Modern Production Technologies, British Sulphur Publishing, London, 1997, Chapter 3—Methanol, pp. 69-101, ISBN 1 873387 26 1.

* cited by examiner

*Primary Examiner*—Sikarl A Witherspoon
(74) *Attorney, Agent, or Firm*—David M. Weisberg

(57) ABSTRACT

This invention is directed to a reactor and process for producing methanol. The reactor includes utilizes a plurality of beds of methanol synthesis catalyst in series to form methanol product from synthesis gas (syngas). A liquid layer continuously flows across the top of each catalyst bed, with one or more conduits (e.g., downcomers) that collect the flowing liquid and flow the collected liquid by gravity down to the next bed of catalyst in series. The downcomers are sealed so that vapor does not pass upwardly through the downcomers.

11 Claims, 1 Drawing Sheet

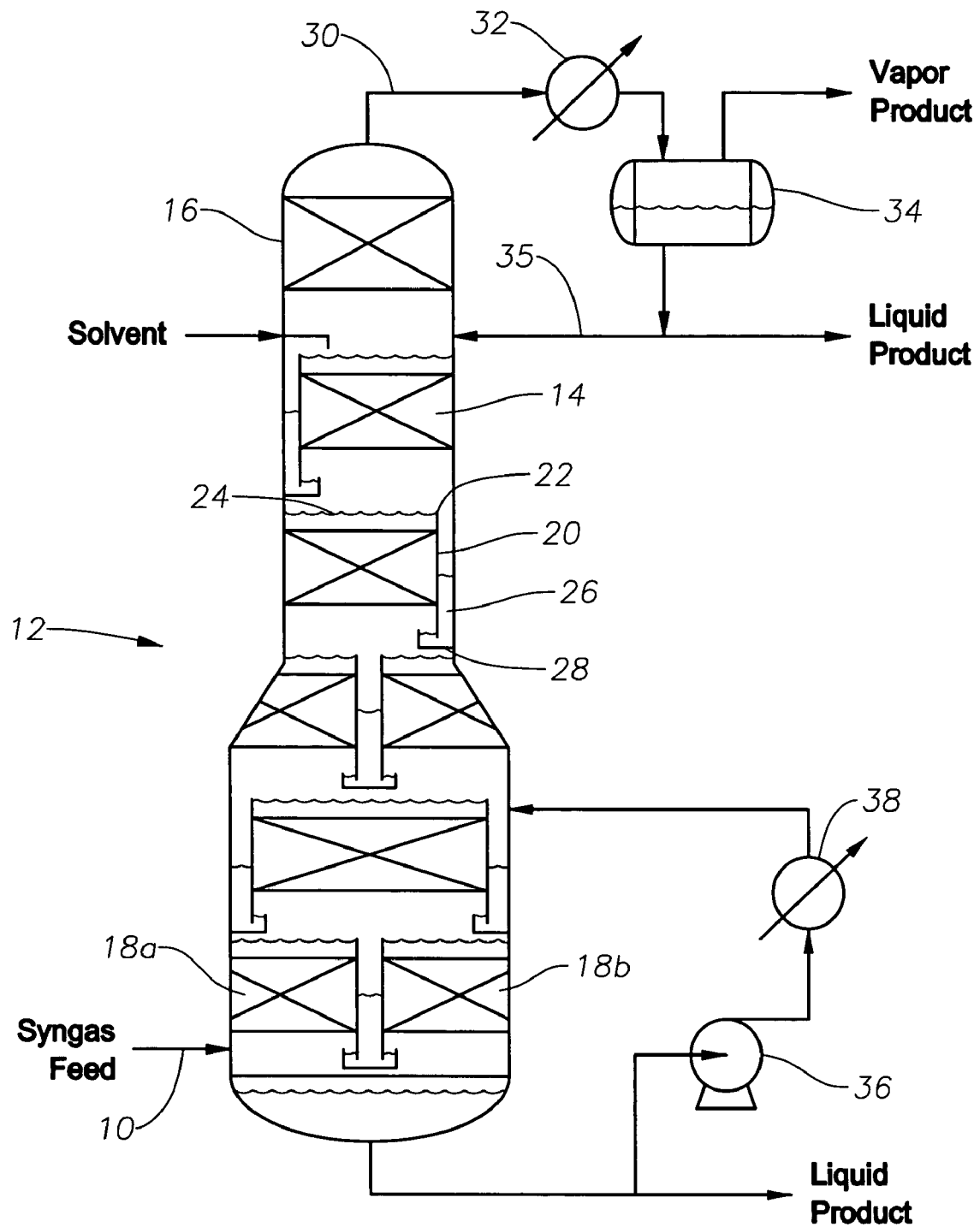

1

REACTOR AND PROCESS FOR PRODUCING METHANOL

CROSS REFERENCE TO RELATED APPLICATION

This claims the benefit of and priority from U.S. Ser. No. 60/816,409, filed Jun. 26, 2006. The above application is fully incorporated herein by reference.

FIELD OF THE INVENTION

This invention relates to the production of methanol. In particular, this invention relates to the production of methanol using countercurrent flow of liquid and gases through a series of methanol synthesis catalyst reaction beds

BACKGROUND OF THE INVENTION

In general, the methanol synthesis process predominantly relies on synthesis gas (syngas) as feed components. Syngas generally contains carbon monoxide and hydrogen. Carbon dioxide and nitrogen can also be present. Methanol production using syngas basically involves the following reactions:

$$CO + 2H_2 \rightarrow CH_3OH \quad (1)$$

$$CO_2 + 3H_2 \rightarrow CH_3OH + H_2O \quad (2)$$

An additional side reaction includes:

$$CO + H_2O \leftrightarrow CO_2 + H_2 \quad (3)$$

Methanol synthesis is a strongly exothermic and equilibrium-limited reaction. Increases in reaction temperature tend to disfavor methanol formation, and tend to deactivate some of the more commonly used copper based catalysts. Thus, control of equilibrium in this complex reaction scheme is important to maximize the amount of methanol formed.

Adiabatic bed reactor and cooled (i.e., isothermal) reactors are commonly used for methanol synthesis. Adiabatic bed reactors typically have several fixed catalyst beds in series, and the temperature is controlled with heat exchangers between beds or by introducing cold synthesis gas between beds. Isothermal reactors typically have a bundle of tubes filled with catalyst, and use water to cool the tubes as the reaction takes place.

U.S. Pat. No. 4,968,722 discloses the use of multiple reactors in series in the manufacture of methanol. After each reactor, an absorption vessel is used to absorb the methanol from the reactor effluent. Examples of absorbents used include tetra ethylene glycol dimethyl ether (TEGDME), sulfolane, and 18-crown-6.

U.S. Pat. No. 5,219,891 discloses a fluidized bed reactor that is used to make methanol. The reactor has catalyst in a plurality of interconnected fluidized bed sections, and each section is cooled by a heat exchanger. The temperature in the highest section is reduced to below the highest temperature in a lower section.

U.S. Pat. No. 5,449,696 discloses a process for the production of methanol that uses a simulated moving bed. In the process, the carbon monoxide and hydrogen are catalytically reacted to form methanol. The methanol is separated from unreacted carbon monoxide and hydrogen by concurrent adsorption, using the carbon monoxide and hydrogen as the desorbent.

U.S. Pat. No. 6,723,886 discloses a process for the production of methanol in a catalytic distillation unit, or CDU. This patent discloses that a number of stages can be used to achieve a final conversion of CO approaching 100%. The heat of reaction may be removed by removing a portion of the methanol, cooling it, and returning it to the CDU. It is not disclosed how the unreacted reactants are returned to the catalyst zone by distillation, since the syngas components are essentially non-condensable at methanol synthesis conditions.

A variety of reaction processes have been disclosed in an effort to find efficient ways of controlling equilibrium and/or temperatures in the complex methanol reaction process. Additional process schemes are still desired in order to maximize the conversion of CO, $CO_2$ and hydrogen to methanol in much simpler and more effective ways. In particular, more efficient reactor systems are sought.

SUMMARY OF THE INVENTION

This invention provides a reactor and process for producing methanol in a manner that provides for high conversion of syngas in a single pass with excellent control of gas phase compositions and reaction temperatures. The reactor and process enable the reaction to be carried out at relatively low temperatures and allows for efficient recovery of the methanol product.

According to one aspect of the invention, there is provided a multistage fixed bed methanol synthesis reactor. The reactor includes a reaction vessel and a plurality of fixed methanol synthesis catalyst reaction beds located within the reaction vessel. The catalyst beds are supported by a respective grid, and there is at least one upper and at least one lower reaction bed. There are also a series of reaction beds located between the at least one upper and at least one lower bed. The series of reaction beds have at least one downcomer extending through or along side each reaction bed, with the downcomer being internal to the reactor. Each downcomer has an upper lip positioned to form a liquid layer above each associated reaction bed, and each downcomer extends below each associated reaction bed into a liquid seal. The liquid seal seals off vapor from passing through the liquid seal and around the associated reaction bed.

The synthesis reactor further includes a gas feed inlet located below the at least one lower reaction bed. In addition, the synthesis reactor includes a methanol product outlet located above the at least one upper reaction bed. A liquid outlet is located below the gas feed inlet.

According to another aspect of the invention, there is provided a process for producing methanol. The process includes flowing gas containing carbon monoxide, carbon dioxide and hydrogen through a gas feed inlet located in a bottom portion of a multistage fixed bed methanol synthesis reactor to contact a plurality of fixed methanol synthesis catalyst reaction beds within the reactor so as to form methanol in the flowing gas. Gas exiting each of the beds flows through separate methanol liquid layers above each reaction bed to remove at least a portion of the methanol from the gas and cool the gas. The separate liquid layers are flowed in an overall counter current direction relative to the flowing gas, and the flowing liquid layers are removed from the beds by flowing the liquid through at least one associated downcomer. Gas reaction product is removed from an upper portion of the reactor, and liquid reaction product is removed from a lower portion of the reactor.

In one embodiment of the invention, at least one liquid seal is formed by having a catch pan below an associated downcomer or by extending at least one downcomer above a reaction bed to a point in which the downcomer is sealed by a liquid level above the reaction bed. In a particular embodiment, at least one liquid seal is formed by having a catch pan below an associated downcomer. In another embodiment, at least one liquid seal is formed by extending at least one downcomer above a reaction bed to a point in which the downcomer is sealed by a liquid level above the reaction bed.

In another embodiment of the invention, at least one grid is a screen, sieve tray, valve tray or bubble cap tray. Preferably, each reaction bed includes a grid on a top portion of the bed.

In one embodiment, the methanol synthesis catalyst includes an oxide of at least one element selected from the group consisting of copper, silver, zinc, boron, magnesium, aluminum, vanadium, chromium, manganese, gallium, palladium, osmium and zirconium.

In yet another embodiment, at least one upper reaction bed has no associated downcomer. Preferably, the reaction vessel includes a reflux liquid inlet below at least one upper reaction bed.

In another embodiment, the reaction vessel includes a pumparound loop with cooler that takes liquid from the liquid outlet and inputs cooled liquid at a point that is below a lower one half of the reaction vessel.

In one more embodiment, each reaction bed that is below the upper reaction bed is sealed from above and below by one or more liquid seals so that vapor can be transported only through the reaction bed.

BRIEF DESCRIPTION OF THE DRAWING

An example of one specific embodiment of this invention in shown in the attached FIGURE, wherein the FIGURE is a flow diagram of a vessel in which gas is flowed across a series of catalyst beds and liquid is flowed in a countercurrent direction to the gas and down to a subsequent catalyst bed by way of a downcomer.

DETAILED DESCRIPTION OF THE INVENTION

I. Methanol Production Using Multiple Catalyst Beds in Series

This invention is directed to a reactor and process for producing methanol. The reactor includes utilizes a plurality of beds of methanol synthesis catalyst in series to form methanol product from synthesis gas (syngas).

The syngas conversion that is achieved according to this invention is very high. The high conversions are achieved by flowing a liquid layer over each catalyst bed so that gas product coming off each bed flows through the liquid layer. The liquid layer acts as a methanol extractant to remove methanol from the gas emerging from the bed of catalyst, leaving any unreacted synthesis gas component behind, and also acts to cool the gas. This cooled gas is then sent to the next bed of catalyst to continue the methanol production reaction, and similar extraction using a liquid layer is repeated, until the reaction is essentially complete. The absorption of methanol into the liquid phase upon leaving each catalyst bed removes at least a portion, preferably at least a majority, of methanol from the synthesis gas. The synthesis gas flowing to the next catalyst bed is cooler and reduced in methanol concentration, thus providing a renewed thermodynamic driving force to allow further conversion of the syngas.

The synthesis gas contains in greater part carbon oxides, such as carbon monoxide, and hydrogen. As these components are flowed through a bed of catalyst, they are converted to methanol. The methanol is formed in the gas phase as the syngas flows through the bed of catalyst.

In one embodiment of the invention, the process involves flowing gas containing synthesis gas components through a plurality of beds of methanol synthesis catalyst. At least 3, preferably at least 5, and most preferably at least 10 beds of methanol synthesis catalyst are used. Preferably in such an embodiment, as the overall conversion of the syngas components progresses, the temperature profile as the gas flows through the plurality of beds of methanol synthesis catalyst remains fairly consistent. On an average linear basis, i.e., from one bed to the next, the average temperature of each bed changes very little. In one embodiment, the average temperature of each bed in a linear arrangement or profile differs from one another in a range of from 0° C. to 10° C., preferably from 0° C. to 5° C., and more preferably from 0° C. to 3° C.

In one embodiment, the reaction is an exothermic reaction. In a preferred embodiment of exothermically converting syngas components to methanol, the gas exits each bed at a temperature of at least 190° C., preferably at least 200° C., and more preferably at least 210° C. The methanol content of the gas exiting any one bed will be higher than that of the gas that entered that particular bed. Preferably, the methanol concentration of the gas exiting each bed is at least 50 mol %, preferably at least 55 mol %, and more preferably at least 60 mol %. This enriched gas stream is contacted with the liquid layer that is flowing across a top portion of the catalyst bed. This contacting cools the gas, absorbing some of the methanol into the liquid phase. The gas leaving the contacting step is now at about the same temperature and methanol concentration as it was in the feed to the previous bed. The quantity of syngas, however, has been reduced because some of the syngas was converted to methanol. These series of steps are then repeated several more times, each time increasing the conversion of syngas. The number of catalyst beds and liquid contacting stages, along with control of the temperatures, space velocities, and pressure, determines the ultimate level of conversion of syngas through the reactor system.

In this invention, it is preferred to maximize the conversion at each bed of catalyst so as to approach equilibrium as closely as possible. The approach to equilibrium conversion can be expressed as an approach temperature to an equilibrium composition. For any given mixture of syngas reactants and methanol product, a temperature can be calculated where the thermodynamic driving force for further reaction is zero. The difference between this calculated equilibrium temperature and the actual process temperature is the approach to equilibrium. A low approach to equilibrium is particularly desirable. Preferably, the reaction process is carried out at an approach to equilibrium temperature of not greater than 15° C., more preferably not greater than 10° C., and most preferably not greater than 5° C.

In one embodiment equilibrium temperature is controlled by controlling weight hourly space velocity, methanol content in the feed to one or more catalyst beds, the actual reaction temperature, the reactor pressure, or any combination thereof. In such an embodiment, the extent of conversion at equilibrium in a catalyst bed is favored at lower space velocities, lower temperatures, and lower product (methanol) concentrations in the feed to the one or more catalyst beds. In one preferred embodiment, the weight hourly space velocity (WHSV) through each bed is not greater than 100 $hr^{-1}$, preferably not greater than 50 $hr^{-1}$, and more preferably not greater than 10 $hr^{-1}$. In another embodiment, the methanol content in the gas being sent to each reactor bed is not greater than 60 mol %, preferably not greater than 55 mol %, and more preferably not greater than 50 mol %. In yet another embodiment, the average temperature of each bed is not greater than 240° C., preferably not greater than 230° C., and more preferably not greater than 220° C.

This invention maximizes conversion at each catalyst bed by flowing the gas exiting the previous catalyst bed through a liquid layer that both cools the flowing gas and extracts at least a portion of the methanol. As the methanol concentration of the gas is removed and the gas is cooled, additional synthesis gas components (i.e., carbon monoxide and hydrogen, and, optionally, carbon dioxide) can be more easily converted to methanol. In one embodiment, the average temperature of the cooled gas (i.e., the gas flowed across the liquid layer and exits the liquid layer) is not greater than about 210° C., preferably not greater than about 200° C., and more preferably not greater than about 190° C. In another embodiment, the methanol content of the cooled gas is not greater than about 60 mol %, preferably not greater than about 55 mol %, and more preferably not greater than about 50 mol %.

Because the sequential reaction and extraction steps of this process can be carefully controlled, the final conversion of syngas is high. Preferably, the reaction process is continued until overall conversion of CO or $CH_4$ is at least about 50%, more preferably at least about 60%, and most preferably at least about 75%.

The liquid layer that is used to cool the gas and extract methanol can be any composition effective to absorb methanol from the gas phase into the liquid phase. Preferably, the liquid layer contains methanol that has been removed from the gas that has been produced. It is particularly preferred to flow the liquid in an overall countercurrent direction relative to the flowing gas. As the liquid continues toward its ultimate direction, it will become more enriched in methanol (unless methanol itself is used as the absorbing liquid, in which case the composition does not substantially change). At a final desired stage in the reaction process, the methanol product is then recovered. If desired, however, methanol can be recovered from any one or more of the liquid layers as they are flowed in their countercurrent direction.

It is particularly desirable for the liquid to minimize contact with the catalyst and unreacted syngas at the same time. The presence of liquid methanol on the catalyst will reduce the potential conversion of syngas to methanol. It is also possible for some of the methanol to undergo the reverse reaction and decompose back to syngas.

According to this invention, the liquid layer continuously flows across the top of each catalyst bed. One or more conduits (e.g., downcomers) are included in the reactor housing the beds such that the conduits collect the flowing liquid and allow the liquid to flow by gravity down to the next bed of catalyst in series. The downcomers are sealed so that vapor does not pass upwardly through the downcomers. This provides an efficient way to move all of the vapor in the reactor in an upward direction through the catalyst beds and the effluent from each catalyst bed to flow through a liquid layer. This type of liquid flow, e.g., across each catalyst bed and down through an associated downcomer, minimizes contact with the catalyst and unreacted syngas at the same time.

Liquid is substantially prevented from flowing down through the bed by selecting a gas velocity that achieves a pressure drop through the catalyst bed of at least 0.01 psi/ft (0.23 kPa/m) of bed height, preferably at least 0.05 psi/ft (1.1 kPa/m) of bed height, and more preferably at least 0.1 psi/ft (2.3 kPa/m) of bed height. This pressure drop can be calculated by those skilled in the art by means of the Ergun equation (see for example, Bennett & Myers, *Momentum, Heat, and Mass Transfer*, 2nd Ed. McGraw Hill, New York (1974)).

The reactor of this invention includes a plurality of fixed methanol synthesis catalyst reaction beds. Each bed is supported by respective grid, which is generally a support with openings small enough to prevent catalyst from falling through the grid, but large enough to enable vapor to pass upwardly through the associated catalyst bed. Examples of such grids include screens, sieve trays, valve trays, bubble cap trays or any standard type of distillation column tray. Each bed can also include a grid on the top portion of the bed if desired.

Each reaction bed is a fixed bed, meaning that the methanol synthesis catalyst supported on each grid does not move. Preferably, the beds do not include packing materials. Thus, the bed density is essentially that of the catalyst bulk density itself. Bulk density is considered the density of the settled packed bed, including the interstitial voids between particles. In other words, the bulk density is the density of the catalyst bed divided by the volume of the bed. Such catalysts typically have a bulk density of from 40 $lb/ft^3$ to 60 $lb/ft^3$.

The reactor of this invention includes a plurality of reaction beds, with at least one upper and at least one lower bed. A series of reaction beds are located between the at least one upper and at least one lower bed. Each bed preferably includes a conduit to bypass the downflowing liquid from directly contacting the catalyst in the bed. One method of bypassing the liquid is to use a downcomer that extends through or along side the bed such that liquid downflow does not contact the catalyst bed. The downcomers are preferably arranged to form a seal at the bottom of the downcomer to prevent upflowing vapors from bypassing the catalyst bed. At least one downcomer extends through or along side at least one reaction bed, with the downcomer being internal to the reactor. Preferably, the downcomer has an upper lip positioned to form a liquid layer above the associated reaction bed. This lip can be of any shape and form as long as the lip functions to provide a liquid layer above its associated reaction bed.

Each downcomer extends below each associated reaction bed into a liquid seal. This liquid seal is actually a liquid barrier that seals off vapor from passing through the liquid seal and around the associated reaction bed. Such a seal forces upward moving vapor in the reactor to move upwardly through each reaction bed. Liquid seals can be formed in a variety of ways. For example, at least one liquid seal is formed by having a catch pan below an associated downcomer. As another example at least one liquid seal can be formed extending at least one downcomer above a reaction bed to a point in which the downcomer is sealed by a liquid level above the next reaction bed in series.

The series beds can have one or more than one downcomer. Each bed is sealed to the passage of vapor, except to the extent that vapor is able to pass through the catalyst bed portion only through the bed itself. The downcomers can be any of a variety of shapes. Non-limiting examples include flat vertical partitions or circular conduits.

It is not necessary, however, that all reactor beds include a downcomer. In particular, the upper reactor needs no downcomer. In such a case, each reaction bed below the upper reaction bed is sealed from above and below by one or more liquid seals so that vapor can be transported only through the reaction bed. Typically, the upper reaction bed does not include a downcomer, as liquid from above that stage typically comes from a condenser and/or reflux line or system, and which provides sufficient sealing to prevent vapor from bypassing the upper bed through the liquid line.

The reactor vessel itself can be of any dimension appropriate for conversion of syngas feed components to methanol product. In one embodiment, the overall reactor diameter decreases from the bottom to the top of the reactor so as to maintain a relatively constant upward vapor rate. In another alternative embodiment, the reactor has at least two sections with each section arranged vertically to one another, and each higher vertical section has a diameter smaller than the next lower vertical section.

Methanol product is withdrawn from the reactor in both vapor and liquid form. At the top of the reactor, the product is in vapor form. This vapor can be cooled, thereby forming a condensed overhead stream and a vapor stream. All or a portion of the condensed overhead stream can be returned to the reaction vessel as coolant. In one embodiment, the reaction vessel includes a reflux liquid inlet below an upper reaction bed, and the condensed overhead is returned to the reaction vessel through the reflux liquid inlet.

Liquid is withdrawn from the bottom of the reactor that contains methanol product. A portion of this liquid can be cooled and used to provide intermediate cooling to the reactor. This type of cooling can be obtained through a pumparound loop in which the liquid portion is pumped through a cooler and back around to the reactor. In one embodiment, the reaction vessel includes a pumparound loop with cooler that takes liquid from the liquid outlet of the vessel and inputs cooled liquid at a point that is below a lower one half of the reaction vessel.

An extractant or solvent can be added to the methanol layer so as to enhance or suppress the volatility of the methanol being removed from the gas streams or as aids in extracting the methanol from the gases. Extractants which can be used in this invention are liquids at 1 atm. These extractants also desirably have an average boiling point at atmospheric pressure of at least 100° F. (38° C.), preferably at least 120° F. (49° C.), and more preferably at least 150° F. (66° C.). Average boiling point, as defined herein, takes into account the boiling point of each compound in the extractant on a weight average basis. For example, an extractant containing 90 wt. % of a compound having a boiling point of 100 degrees and 10 wt. % of a compound having a boiling point of 200 degrees would have an average boiling point of 110 degrees. The extractants are also desirably polar compositions. Examples of such compositions include at least one composition selected from the group consisting of water, monohydric alcohols, and polyhydric alcohols. Preferred monohydric alcohols, in addition to methanol, include ethanol and propanol. Preferred polyhydric alcohols include glycols. Preferred glycols include ethylene glycol and tri-ethylene glycol. Preferably, the extractant or solvent is introduced in an upper portion of the reactor.

In order to achieve an overall high conversion of syngas components in the process, it is desirable to operate with a decreasing temperature profile as the syngas travels up the column. The temperature should be somewhat higher at the bottom where the concentration of reactants is high, as reaction rates will be higher and the equilibrium conversion constraints are not so great. The temperature should be somewhat lower towards the top of the column where reactants have been consumed and the concentration of inerts builds up. Lower temperatures allow higher thermodynamic conversions to occur in the diluted reaction mixture. The average bed temperature in the first (bottom) bed is preferably at least 5° C. hotter than the last (top) bed, more preferably at least 10° C. hotter, and most preferably at least 15° C. hotter.

The liquid that is used to form the liquid layers used in this invention not only absorbs methanol but cools the product gases as they flow through each layer. As stated above, the liquid is preferably maintained at a temperature such that the gases that are flowed through each catalyst bed exhibit an overall temperature profile in which the average temperature of each catalyst bed decreases in the direction of gas flow. Thus, each liquid layer is at an average temperature that cools the gas flowing through it. In one embodiment, each liquid layer is maintained at an average temperature of not greater than 250° C. Preferably, each liquid layer is at an average temperature of not greater than 240° C., more preferably not greater than 230° C., and most preferably not greater than 220° C.

In another embodiment, none of the beds of methanol synthesis catalyst has an inlet temperature greater than 240° C. Preferably, none of the beds of methanol synthesis catalyst has an inlet temperature greater than 220° C.

In this invention, it is preferred that each catalyst bed is arranged in series. In particular embodiments, it is also preferred that, on average, no catalyst bed has an inlet temperature greater than that of the previous bed in series. That is, on average the temperature decreases as the gas flows up the column, but on occasion, the temperature profile can be discontinuous due to the number and locations of pumparound loops that are used to cool certain beds. Thus, in one embodiment, at least some of the methanol is withdrawn from the column, cooled, and pumped back into the column at a desired location to cool any bed below the location at which the cooled methanol is injected. More than one pumparound can be used.

A wide variety of pressures can be accommodated in carrying out the process of the invention. Preferably, the gases and liquid layers are flowed in one or more vessels, each at a pressure of at least 30 bar, more preferably at least 50 bar, still more preferably at least 70 bar, and most preferably at least 90 bar. Preferably, the gases and liquid layers are flowed in one or more vessels, each at a pressure of not greater than 200 bar, preferably not greater than 150 bar, and more preferably not greater than 120 bar.

II. Process Feed

As in a typical methanol producing process, synthesis gas (syngas) is used in the feed as feed in the initial reaction step of this invention. Desirably, the synthesis gas used in the initial reaction step has a molar ratio of hydrogen ($H_2$) to carbon oxides ($CO+CO_2$) in the range of from about 0.5:1 to about 20:1, preferably in the range of from about 1:1 to about 10:1. In another embodiment, the synthesis gas has a molar ratio of hydrogen ($H_2$) to carbon monoxide (CO) of at least 2:1. Carbon dioxide is optionally present in an amount of not greater than 50% by weight, based on total weight of the synthesis gas, and preferably less than 20% by weight, more preferably less than 10% by weight.

Desirably, the stoichiometric molar ratio is sufficiently high so as maintain a high yield of methanol, but not so high as to reduce the volume productivity of methanol. Preferably, the synthesis gas fed to the methanol synthesis process has a stoichiometric molar ratio (i.e., a molar ratio of $(H_2-CO_2)/(CO+CO_2)$) of from about 1.0:1 to about 2.7:1, more preferably from about 1.5 to about 2.5, more preferably a stoichiometric molar ratio of from about 1.7:1 to about 2.5:1.

III. Catalyst

Preferably, the methanol synthesis catalyst used in the process of this invention includes an oxide of at least one element selected from the group consisting of copper, silver, zinc, boron, magnesium, aluminum, vanadium, chromium, manganese, gallium, palladium, osmium and zirconium. More preferably, the catalyst is a copper based catalyst, more preferably in the form of copper oxide.

In another embodiment, the catalyst used in the methanol synthesis process is a copper based catalyst, which includes an oxide of at least one element selected from the group consisting of silver, zinc, boron, magnesium, aluminum, vanadium, chromium, manganese, gallium, palladium, osmium and zirconium. Preferably, the catalyst contains copper oxide and an oxide of at least one element selected from the group consisting of zinc, magnesium, aluminum, chromium, and zirconium. More preferably, the catalyst contains oxides of copper and zinc.

In yet another embodiment, the methanol synthesis catalyst comprises copper oxide, zinc oxide, and at least one other oxide. Preferably, the at least one other oxide is selected from the group consisting of zirconium oxide, chromium oxide, vanadium oxide, magnesium oxide, aluminum oxide, titanium oxide, hafnium oxide, molybdenum oxide, tungsten oxide, and manganese oxide.

In various embodiments, the methanol synthesis catalyst comprises from about 10 wt % to about 70 wt % copper oxide, based on total weight of the catalyst. Preferably, the methanol synthesis contains from about 15 wt % to about 68 wt % copper oxide, and more preferably from about 20 wt % to about 65 wt % copper oxide, based on total weight of the catalyst.

In one embodiment, the methanol synthesis catalyst comprises from about 3 wt % to about 30 wt % zinc oxide, based on total weight of the catalyst. Preferably, the methanol synthesis catalyst comprises from about 4 wt % to about 27 wt % zinc oxide, more preferably from about 5 wt % to about 24 wt % zinc oxide.

In embodiments in which copper oxide and zinc oxide are both present in the methanol synthesis catalyst, the ratio of copper oxide to zinc oxide can vary over a wide range. Preferably in such embodiments, the methanol synthesis catalyst comprises copper oxide and zinc oxide in a Cu:Zn atomic ratio of from about 0.5:1 to about 20:1, preferably from about 0.7:1 to about 15:1, more preferably from about 0.8:1 to about 5:1.

In one embodiment, this invention involves direct oxidation of methane to methanol. In such an embodiment, a catalyst is used that is capable of enhancing the production and/or propagation of free radicals. Alternatively, no catalyst is employed, and the reaction bed is preferably an empty section of the column where the methane and oxygen are given residence time to react.

IV. Recovery and Further Processing of Methanol Product

After reaction, the methanol product can be recovered and used "as is," or it can be further processed if desired. Processing can be accomplished using any conventional means. Examples of such means include distillation, selective condensation, and selective adsorption. Process conditions, e.g., temperatures and pressures, can vary according to the particular methanol composition desired. It is particularly desirable to minimize the amount of water and light boiling point components in the methanol composition, but without substantially reducing the amount of methanol present.

In one embodiment, the recovered methanol product is sent to a let down vessel so as to reduce the pressure to about atmospheric or slightly higher. This let down in pressure allows undesirable light boiling point components to be removed from the methanol composition as a vapor. The vapor is desirably of sufficient quality to use a fuel.

In another embodiment, the recovered methanol product is sent from the methanol synthesizing unit or vessel to a distillation system. The distillation system contains one or more distillation columns which are used to further separate the desired methanol composition from water and hydrocarbon by-product streams. Desirably, the methanol composition that is separated from the crude methanol comprises a majority of the methanol contained in the methanol product prior to separation.

In one embodiment, the distillation system includes a step of treating the recovered methanol product steam being distilled so as to remove or neutralize acids in the stream. Preferably, a base is added in the system that is effective in neutralizing organic acids that are found in the methanol stream. Conventional base compounds can be used. Examples of base compounds include alkali metal hydroxide or carbonate compounds, and amine or ammonium hydroxide compounds. In one particular embodiment, about 20 ppm to about 120 ppm w/w of a base composition, calculated as stoichiometrically equivalent NaOH, is added, preferably about 25 ppm to about 100 ppm w/w of a base composition, calculated as stoichiometrically equivalent NaOH, is added.

Examples of distillation systems include the use of single and two column distillation columns. Preferably, the single columns operate to remove volatiles in the overhead, methanol product at a high level, fusel oil as vapor above the feed and/or as liquid below the feed, and water as a bottoms stream.

In one embodiment of a two column system, the first column is a "topping column" from which volatiles are taken overhead and methanol liquid as bottoms. The second is a "rectifying column" from which methanol product is taken as an overhead stream or at a high level, and water is removed as a bottoms stream. In this embodiment, the rectifying column includes at least one off-take for fusel oil as vapor above the feed and/or as liquid below the feed.

In another embodiment of a two column system, the first column is a water-extractive column in which there is a water feed introduced at a level above the crude methanol feed level. It is desirable to feed sufficient water to produce a bottoms liquid containing over 40% w/w water, preferably 40% to 60% w/w water, and more preferably 80% to 95% w/w water. This column optionally includes one or more direct fusel oil side off-takes.

In yet another embodiment, the distillation system is one in which an aqueous, semi-crude methanol is taken as liquid above the feed in a single or rectifying column. The semi-crude methanol is passed to a rectifying column, from which methanol product is taken overhead or at a high level. Preferably, water or aqueous methanol is taken as a bottoms stream.

Alternatively, undesirable by-products are removed from the crude methanol stream from the methanol synthesis reactor by adsorption. In such a system, fusel oil can be recovered by regenerating the adsorbent.

V. Use of the Methanol Composition in the Manufacture of Olefins

The methanol product composition of this invention can be used as feed for any conventional process. Examples of such uses include the manufacture of methyl tertiary butyl alcohol (MTBE) for use in reformulated gasolines and oxygenated fuels; the use of methanol as a fuel for fuel cells, use as feedstock to make olefins, and for use in making acetic acid and formaldehyde.

The methanol product stream of this invention is particularly suited for conversion to olefins, particularly ethylene and/or propylene. The methanol product stream can be fed directly to an olefin conversion process or it can be transported in large quantities over great distances and converted to olefins.

According to this invention, the methanol product can be produced in large scale quantities for conversion to olefins, which is of great advantage for further conversion of the olefins to polyolefins such as polyethylene and polypropylene. Advantageously, this invention allows for at least 100, 000 metric tons of methanol product per year. Preferably, production is at least 500,000 metric tons per year, more preferably at least 1 million metric tons per year, and most preferably at least 2 million metric tons per year.

In one embodiment, the methanol stream of the invention is separated from a crude methanol stream, and transported to a location geographically distinct from that where the methanol composition was separated from the crude methanol stream. Preferably, the methanol composition of this invention is loaded into a vessel, and the vessel is transported over a body of water to a storage facility. The methanol can be easily transported at least 100, 500 or 1,000 miles or more. Once arriving at the storage facility, the methanol composition is delivered to a storage tank. From the storage tank, the methanol composition is ultimately sent to an olefin conversion unit for conversion to an olefin product. The methanol composition is preferably, loaded onto a ship, with the ship able to contain at least 20,000 tons, preferably at least 40,000 tons, and more preferably at least 80,000 tons.

An advantage of being able to transport the methanol composition is that the units which produce the methanol do not have to be located in close geographic proximity to the olefin conversion unit. This makes it possible to use remote gas reserves. These remote gas reserves would be used as feed for the methanol manufacturing facility. The methanol made at these remote sites can then be easily transported to a suitable location for conversion to olefins. Since olefins and polyolefins (i.e., plastics) demands are typically low at the remote gas sites, there will generally be a desire to transport methanol to high olefins and plastic demand areas. Methanol is routinely transported in vessels that are similar to those that transport crude oil and other fuels. Examples of locations of remote gas reserves include the coastline of west Africa, northwest Australia, in the Indian Ocean, and the Arabian Peninsula. Examples of locations of preferred sites to convert methanol to other products such as olefins include the U.S. Gulf coast and northwest Europe.

VI. Examples of Different Embodiments

An example of one embodiment of this invention is shown in the FIGURE. According to the embodiment in the FIGURE, syngas containing carbon monoxide, carbon dioxide and hydrogen is flowed through a gas feed inlet 10 located in a bottom portion of a multistage fixed bed methanol synthesis reactor 12. The syngas components contact a plurality of fixed methanol synthesis catalyst reaction beds (exemplified by bed 14) within the reactor 12 so as to form methanol in the upwardly flowing gas. The plurality of reaction beds includes at least one upper reaction bed 16 and at least one lower reaction bed 18a, 18b.

As shown in the FIGURE, a series of reaction beds is located between the upper reaction bed 16 and the lower reaction bed 18a, 18b. The series of reaction beds located between the between the upper reaction bed 16 and the lower reaction bed 18a, 18b have downcomers (exemplified by downcomer 20) extending along side each reaction bed and internal to the reactor 12. The downcomer 20 is shown to have a lip 22 that forms a liquid level 24 above its associated catalyst bed. The downcomer 20 extends into a liquid seal, which is formed in this embodiment by the use of a catch pan 28.

The upwardly flowing reaction or feed gas exits each of the beds through separate methanol liquid layers above each reaction bed to remove at least a portion of the methanol from the gas and cool the gas. The separate liquid layers are flowed in an overall counter current direction relative to the flowing gas, since the liquid ultimately flows in a downward direction through each downcomer.

Gas reaction product is removed from an upper portion of the reactor by way of a line 30 and cooled by a cooler to form a vapor and liquid product, which is collected in separator 34. The vapor product is removed as an overhead vapor stream from the separator, and liquid product is either sent back to the reactor 12 through a reflux inlet line 35 to further cool the reactor beds or removed as liquid product.

A majority of the liquid product is removed at a lower portion of the reactor 12. At least a portion of the liquid product can be sent through a pumparound loop by way of a pump 36 and cooled by passing through a cooler 38. The cooled liquid is then returned to a lower portion of the reactor 12 to further cool the reactor beds.

In this embodiment, solvent is also added in an upper portion of reactor 12. Solvent addition need not be continuously applied, but can assist in further recovering methanol vapor product through absorption in the liquid layers.

The principles and modes of operation of this invention have been described above with reference to various exemplary and preferred embodiments. As understood by those of skill in the art, the overall invention, as defined by the claims, encompasses other preferred embodiments not specifically enumerated herein.

What is claimed is:

1. A process for producing methanol, comprising:

flowing gas containing carbon monoxide, carbon dioxide and hydrogen through a gas feed inlet located in a bottom portion of a multistage fixed bed methanol synthesis reactor to contact a plurality of fixed methanol synthesis catalyst reaction beds within the reactor so as to form methanol in the flowing gas, wherein the plurality of reaction beds includes at least one upper and at least one lower bed as well as a series of reaction beds located between the at least one upper and at least one lower bed, with the series of reaction beds located between the at least one upper and at least one lower bed having at least one downcomer extending through or along side each reaction bed and internal to the reactor, flowing gas exiting each of the beds through separate methanol liquid layers above each reaction bed to remove at least a portion of the methanol from the gas and cool the gas, wherein the separate liquid layers are flowed in an overall counter current direction relative to the flowing gas;

removing the flowing liquid layers from the beds by flowing the liquid through at least one associated downcomer, wherein each downcomer has an upper lip positioned to form an associated methanol liquid layer above each associated reaction bed and each downcomer extends below each associated reaction bed into a liquid seal to seal off vapor from passing through the liquid seal and around the associated reaction bed;

removing gas reaction product from an upper portion of the reactor; and removing liquid reaction product from a lower portion of the reactor.

2. The process of claim 1, wherein at least one liquid seal is formed by having a catch pan below an associated downcomer or by extending at least one downcomer above a reaction bed to a point in which the downcomer is sealed by a liquid level above the reaction bed.

3. The process of claim 1, wherein at least one liquid seal is formed by having a catch pan below an associated downcomer.

4. The process of claim 1, wherein at least one liquid seal is formed by extending at least one downcomer above a reaction bed to a point in which the downcomer is sealed by a liquid level above the reaction bed.

5. The process of claim 1, wherein at least one grid is a screen, sieve tray, valve tray or bubble cap tray.

6. The process of claim 1, wherein each reaction bed includes a grid on a top portion of the bed.

7. The process of claim 1, wherein the methanol synthesis catalyst includes an oxide of at least one element selected from the group consisting of copper, silver, zinc, boron, magnesium, aluminum, vanadium, chromium, manganese, gallium, palladium, osmium and zirconium.

8. The process of claim 1, wherein the at least one upper reaction bed has no associated downcomer.

9. The process of claim 1, wherein a reflux liquid is input to the reactor at a point below the at least one upper reaction bed.

10. The process of claim 1, wherein at least a portion of the liquid reaction product is sent through a pumparound loop with cooler to cool the liquid and the cooled liquid is input to the reactor at a point below a lower one half of the reaction vessel.

11. The process of claim 1, wherein each reaction bed below the at least one upper reaction bed is sealed from above and below by one or more liquid seals so that vapor can be transported only through the reaction bed.

* * * * *